(12) United States Patent
Tzeng et al.

(10) Patent No.: US 6,268,183 B1
(45) Date of Patent: Jul. 31, 2001

(54) METHOD OF PURIFYING THURINGIENSIN

(75) Inventors: Yew-Min Tzeng; Bing-Lan Liu; Shyuan-Shuenn Huang, all of Hualien Hsien; Cheng-Ming Liu, Taipei; Hung-Yieng Tsun, Chiai Hsien, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/587,151

(22) Filed: Jun. 2, 2000

(30) Foreign Application Priority Data

Jan. 28, 2000 (TW) .............................. 089101464

(51) Int. Cl.$^7$ .................................. C12P 19/26
(52) U.S. Cl. ................ 435/84; 424/93; 424/115; 424/467; 435/41; 435/72; 435/87; 435/89; 435/122; 435/135; 435/136; 435/137; 435/252.31; 435/252.5; 514/47; 514/252; 514/255; 514/264; 536/26.21; 536/28.4; 536/28.5; 536/28.53; 536/28.54
(58) Field of Search .............................. 424/93, 467, 115; 435/41, 72, 84, 87, 89, 122, 135, 136, 137, 252.5, 252.31; 514/47, 252, 264, 255; 536/26.21, 284, 28.5, 28.53, 28.54

(56) References Cited

U.S. PATENT DOCUMENTS 5,859,235 * 1/1999 Liu et al. .......................... 536/28.53
5,976,563 * 11/1999 Liu et al. .............................. 424/405

OTHER PUBLICATIONS

Kim. Y. T. et al., The beta Exotoxins of *Bacillus thuringiensis*. I. Isolation and Characterization, 1970, J. Inv. Pathol., 15: 100–108.*

Jonson. D.E. et al., Limitations of HPLC for the Detection of beta Exotoxin in Culture Filtrates of *Bacillus thuringiensis*. 1983, Eur. J. Appl Microbiol., Biotechnol., 17:231–234.*

Yew–Min Tzeng et al., *Penicillin–G Enhanced Production of Thuringiensin by Bacillus thuringiensis SP. Darmstadiensis*, Biotechnology Progress, vol. 11, No. 2, pp. 231–234 (1995).

Yew–Min Tzeng et al., *Recovery of Thuringiensin with Cetylpyridinium Chloride Using Micellar–Enhanced Ultrafiltration Process*, Biotechnology Progress, vol. 15, No. 3, pp. 580–586 (1999).

* cited by examiner

Primary Examiner—Francisco Prats
Assistant Examiner—K. C. Srivastava
(74) Attorney, Agent, or Firm—Christensen O'Connor Johnson Kindness PLLC

(57) ABSTRACT

The invention discloses a two-step process for recovery of thuringiensin, comprising adsorbing the thuringiensin from fermentation broth by calcium silicate, and dissociating the thuringiensin by dibasic sodium phosphate. The resulting thuringiensin can be further purified by using semi-preparative HPLC and electrodialysis to remove the excess salts from the recovered thuringiensin solution.

15 Claims, 6 Drawing Sheets

Thuringiensin

Fermentation broth
(supernatant)

Tryptophan

After calcium
silicate adsorbed 0 5 10 15 20 25 30 35 40
Time (min)

Fig. 2

Thuringiensin

Tryptophan 0 5 10 15 20 25 30 35 40
Time (min)

Fig. 3

METHOD OF PURIFYING THURINGIENSIN

BACKGROUND OF THE INVENTION

1. Field of the Invention

The present invention relates to a method of purifying thuringiensin, and more particularly to a method of purifying thuringiensin by using calcium silicate adsorption and dibasic sodium phosphate dissociation processes.

2. Description of the Related Arts

Traditional chemical insecticides are extensively applied in agriculture. However, their toxicity is also harmful to human and livestock, and the dosage used is increasing due to the increasing resistance of the insects to the chemical insecticides. Thus, the use of traditional chemical insecticides not only endangers agricultural workers, but also jeopardizes the health of consumers due to the residual pesticides on crops. Further, the impact of traditional chemical pesticides on the environment is of serious concern. Therefore, an insecticide obtained from nature and possessing high safety and low resistance is a key developing point in the field of insecticides.

Bacillus thuringiensis is a naturally occurring, soil borne organism that has gained a great deal of attention for its ability to express compounds which control certain insect pests. Thuringiensin, one of eight toxins produced by B. thuringiensis, is a metabolic product and a heat-stable β-exotoxin, especially effective for fly control and often referred to as "fly factor". Since the discovery of thuringiensin (McConnell, E. and Richards, A. G., (1959) Can. J. Microbiol. 5:161–168), many aspects of its physical and biochemical properties, modes of action, and insecticidal/acaricidal selectivity have been described (Bond, R. P. M., et al. (1969) Biochem. J. 114:477–488). Thuringiensin ($C_{22}H_{32}N_5O_{19} \cdot H_2O$) is a heat-stable compound with a molecular weight of 701 daltons. Its chemical structure is similar to that of nucleotides. The mechanism of insecticidal action is through inhibition of the production of DNA-dependent RNA polymerase by competition with ATP (Lecadet, M. M. and De Barjac, H., in Davidson, E. W. (Ed.): Pathogenesis of invertebrate microbial disease, pp.293–321, Totowa, N.J., Allanheld and Osmun, 1981). This toxic action generally applies to orders of insects such as Coleoptera, Diptera, Hymenoptera, Isoptera, Lepidoptera, Orthoptera, Neuroptera, Hemiptera and Acari in the families Tetranychidae and Phytoseiidae (Bond, R. P. M., et al. in Burges, H. D. and Hussey, N. W. (Eds.): Microbial control of insects and mites, pp.275–303, London Academic Press, 1971; Hall, I. M., et al. (1971) J. Invertebr. Pathol. 18:359–362; Herbert, D. A. and Harper, J. D., (1986) J. Economic Entomol. 79:592–595; Hoy, M. A. and Ouyang, Y. L., (1987) J. Economic Entomol. 80:507–511). The toxicity of thuringiensin is much less than that of most chemical insecticides. Therefore, it shows great potential to become a very useful insecticide for controlling a wide range of insects.

Recent studies have shown that the production of thuringiensin could be improved by a net-draft-tube modified air-lift reactor (Tzeng, Y. M. and Young, Y. H., (1996) World J. Microbiol. Biotechnol. 12:32–37). During the period of fermentation, penicillin-G may enhance the production (Tzeng, Y. M. and Young, Y. H., (1995) Biotechnol. Prog. 11:231–234). These findings make thuringiensin more practical in terms of mass production. However, a lack of low-cost method for recovery of thuringiensin from fermentation broth has been the major rate-limiting step for industrial application. Traditional membrane ultrafiltration is not only expensive, but also time consuming and inefficient. Tzeng et al. (1999, Biotechnol. Prog. 15:580–586) developed a micellar-enhanced ultrafiltration method to facilitate the efficiency of recovery by using a surfactant and cetylpyridinium chloride (CPC). However, some drawbacks in this method include limited adsorption rate, toxicity of CPC, and micellar complex accumulation within the filter, thereby deteriorating the efficiency of ultrafiltration.

SUMMARY OF THE INVENTION

It is therefore an object of the present invention to provide a process of purifying thuringiensin, comprising the steps of: (a) preparing a sterile and acidic thuringiensin fermentation broth; (b) performing centrifugation of said thuringiensin fermentation broth; (c) adding an adsorbent to the supernatant obtained from step (b), and stirring to form a precipitate of said adsorbent and the thuringiensin; (d) isolating said precipitate by centrifugation; (e) adding a basic de-adsorption agent into said precipitate and vortexing to dissociate the thuringiensin; and (f) recovering and purifying the thuringiensin dissociated from step (e).

In the present invention, calcium silicate is added to the supernatant which is obtained from the thuringiensin fermentation broth by centrifugation, so that the thuringiensin dissolved in the solution can be precipitated by calcium silicate adsorption. After centrifugation, dibasic sodium phosphate is added to the precipitate and vortexed. The thuringiensin can be dissociated by the reaction of dibasic sodium phosphate with calcium silicate. After centrifugation, a preliminarily purified thuringiensin can be obtained.

The thuringiensin purified according to the method of the present invention has advantages of low-cost and quick production. The resulting thuringiensin can be formulated to a powder, thus allowing for easy release of the thuringiensin by adding water.

Another object of the present invention is to provide a high purity thuringiensin which is obtained by further purification using chromatography and electrodialysis, and which can be used as a standard for quantitative analysis.

BRIEF DESCRIPTION OF THE FIGURES

The present invention will be more fully understood and further advantages will become apparent when reference is made to the following description of the invention and the accompanying drawings in which:

FIG. 2 is a micellar electrokinetic capillary electropherogram showing the supernatant of fermentation broth before (upper panel) and after (lower panel) mixed with 2% calcium silicate;

FIG. 3 is a micellar electrokinetic capillary chromatogram showing the thuringiensin dissociated from calcium silicate precipitate by dibasic sodium phosphate;

DETAILED DESCRIPTION OF THE INVENTION

Figure 1:
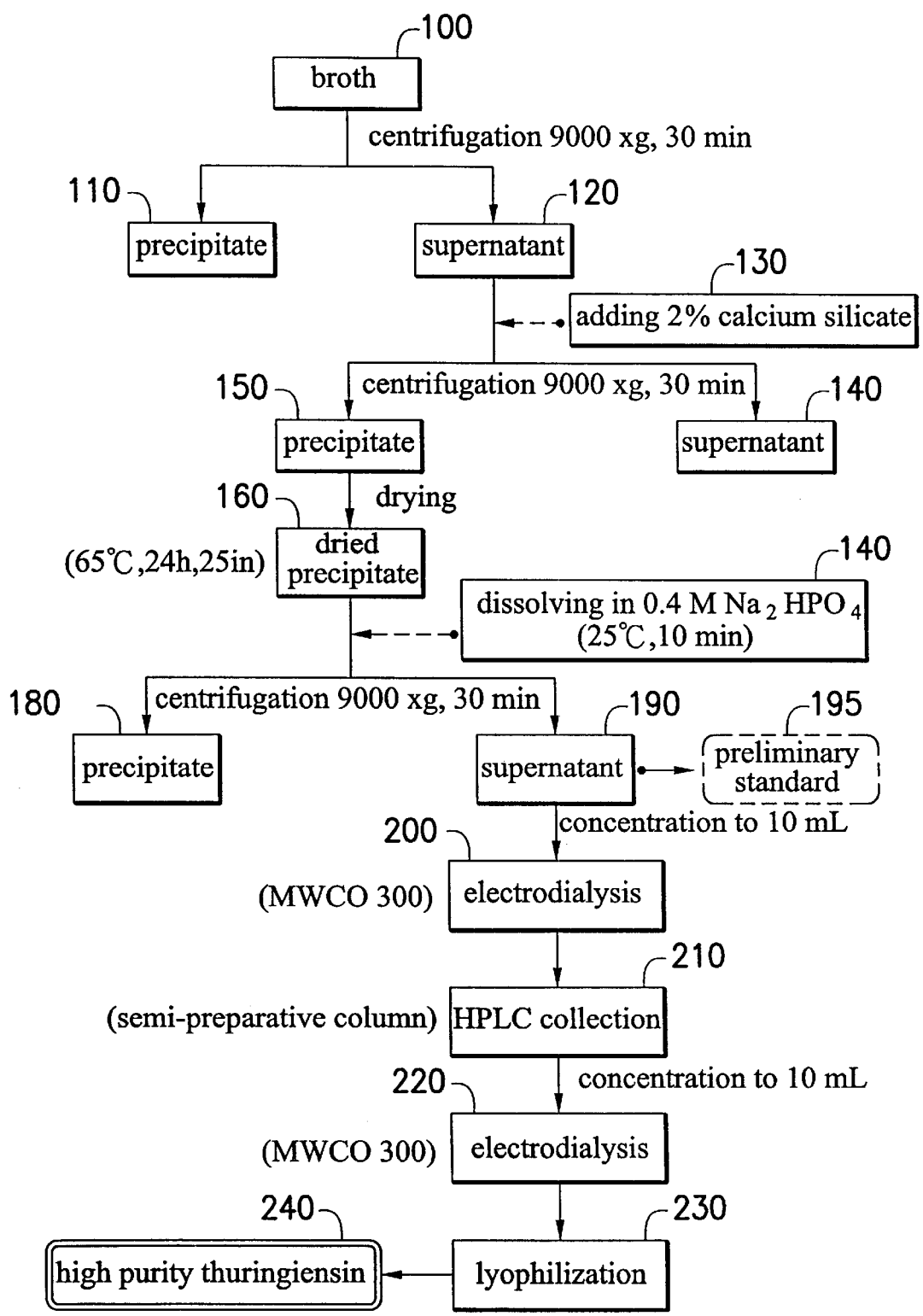
FIG. 1 is a flow chart showing the procedure of purifying thuringiensin according to the present invention.
Figure 4:
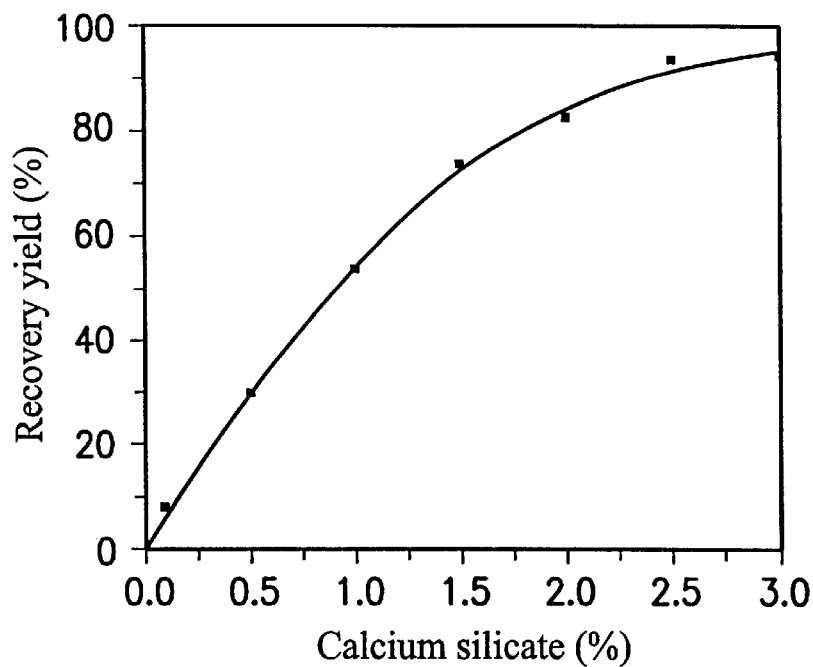
FIG. 4 is a diagram showing the relationship between the amount of calcium silicate and the recovery yield.

In accordance with the present invention, there is provided a process of purifying thuringiensin, comprising the steps of: (a) preparing a sterile and acidic thuringiensin fermentation broth; (b) performing centrifugation of said thuringiensin fermentation broth; (c) adding an adsorbent to the supernatant obtained from step (b), and stirring to form a precipitate of said adsorbent and the thuringiensin; (d) isolating said precipitate by centrifugation; (e) adding a basic de-adsorption agent into said precipitate and vortexing to dissociate the thuringiensin; and (f) recovering and purifying the thuringiensin dissociated from step (e).

Refer to FIG. 1. According to the method of the present invention, the concentration of the thuringiensin in the fermentation broth is ranging from 7 to 10 mg/ml. The amount of the adsorbent added in step (c) ranges from 0.1% to 5% (w/v), preferably from 1% to 3% (w/v). The adsorbent used herein is a compound of calcium silicate including, but not limited to, $Ca_3SiO_3$ or $Ca_2SiO_4$. The pH of the fermentation broth in step (a) is ranging between 4 and 6. The centrifugal condition in step (d) is 9,000×g for 30 minutes. In addition, the amount of the basic de-adsorption agent added in step (e) is 20 volumes of the precipitate. The basic de-adsorption agent used herein is sodium phosphate selected from the group consisting of $Na_2HPO_4$, $Na\text{-}H_2PO_4$ and $Na_3PO_4$, wherein the concentration of the sodium phosphate is ranging from 0.1 to 0.85 M, preferably from 0.4 to 0.6 M. The pH of the solution in step (e) is ranging between 9.0 and 9.5, and the vortexing time in this step is 30 minutes. The recovering step in step (f) comprises performing centrifugation at 9,000×g for 30 minutes, and then concentrating the supernatant obtained from centrifugation. The purifying step in step (f) comprises purifying the concentrated supernatant described above by semi-preparative HPLC to obtain an eluant. The purifying step further comprises the steps of de-salting, concentrating and lyophilizing the eluant purified by HPLC.

Without intending to limit it in any manner, the present invention will be further illustrated by the following examples.

EXAMPLE

Example 1

Purification of Thuringiensin

This example was primarily carried out according to the flow chart shown in FIG. 1. The fermentation broth 100 was from the culture of *B. thuringiensis* subsp. *darmstadiensis* (HD-199), which was received from Dr. H. de Barjac, Insitut Pasteur, Paris. 250 ml of culture broth was sterilized at 121° C. for 20 minutes. After cooling, the broth was centrifuged at 8,820×g for 15 minutes, and the supernatant was collected. The supernatant was then filtered through a cellulose acetate membrane filter (0.45 $\mu$m, Millipore). The method for quantitative analysis of thuringiensin was established by using micellar electrokinetic capillary chromatography (MEKC), P/ACE system, (Model 2100; Beckman Instruments, Fullerton, Calif., USA), controlled by System Gold software (San Ramon, Calif., USA)(Liu, C. M. and Tzeng, Y. M., (1998) *J. Chromatogr. A.* 809:258–263). The concentration of thuringiensin was adjusted to about 8 mg/ml, and then the pH was adjusted to 5.0 by 85% phosphoric acid. The fermentation broth 100 was centrifuged at 9,000×g for 30 minutes and the precipitate 110 was removed to obtain 250 ml of supernatant 120. Afterwards, 2% (w/v) calcium silicate 130 was added to the supernatant 120. After stirring at 150 rpm under room temperature for 1 hour, the supernatant containing calcium silicate was centrifuged at 9,000 ×g for 30 minutes (4° C.). Then, a small volume of supernatant was sampled for quantitative analysis of thuringiensin, and the other supernatant 140 was removed to obtain 8 g of precipitate 150.

The MEKC electrophoretic running buffer contained $Na_2HPO_4$ (20 mM), phosphate borate (20 mM) and sodium dodecyl sulfate (100 mM) with 10% acetonitrile. Electrophoresis was conducted by the P/ACE 2100 under a voltage of 15 kV for 30 to 40 minutes. The dimension of capillary (Polymicro Technologies, Inc., Phoenix, Ariz., USA) was 47 cm×50 $\mu$m I.D. without coating. The UV detection wavelength was set at 254 nm.

Refer to FIG. 2, in which the concentration of thuringiensin in the fermentation broth assessed by MEKC is shown in the upper panel. The thuringiensin peak, located at approximately 24 minutes, was identified by spiking a purified standard, while the tryptophan peak, appearing at approximately 13 minutes, was used as an internal standard for quantitative analysis. The concentration of thuringiensin was 7.5 mg/ml in this specific lot, which was estimated by calculating the absorptive peak area ratio between thuringiensin and tryptophan and then by reduction from the established standard curve (Yuasa, H. et al., (1994) *Chem. Pharm. Bull.* 42:2327–2331). The lower panel of FIG. 2 shows the same broth was mixed with calcium silicate. The thuringiensin was adsorbed, and the amount of thuringiensin which remained in the supernatant was 0.77 mg/ml. The difference between thuringiensin before and after mixing with calcium silicate means that approximately 90% of the thuringiensin was adsorbed by calcium silicate.

To isolate the thuringiensin, precipitate 150 was dried (65° C., 24 h, 25 in) to obtain 5.8 g of crude precipitate 160. A mildly basic sodium phosphate solution 170 (0.4 M $Na_2PO_4$, pH 9.15) was used as de-adsorption agent, and added by 20 volumes of the dried precipitate into the precipitate of calcium silicate-thuringiensin. The mixture was vortexed at room temperature (25° C.) for 10 minutes to dissociate thuringiensin from precipitate. After centrifugation at 9,000×g for 30 minutes, the precipitate 180 was removed. The supernatant 190 (400 ml) containing thuringiensin was collected and quantitatively analyzed for thuringiensin by CE with MEKC mode described above (Referring to FIG. 3). The supernatant 190 containing thuringiensin was used as preliminary standard 195.

Example 2

The Effect of Addition of Calcium Silicate Level on Adsorption

The pH of the filtered supernatant of fermentation broth was adjusted to 5 as described in Example 1, and various amounts of calcium silicate (0.5%, 1.0%, 1.5%, 2.0%, 2.5%, and 3.0%) were added. The mixture was mixed with a rotary shaker in a water bath with temperature set at 30° C., and speed was set at 150 rpm for 30 minutes. The mixture was centrifuged (9,000×g) for 30 minutes, and the precipitate was collected. A small volume of supernatant was kept for monitoring the remaining amount of thuringiensin by CE with MEKC mode.

FIG. 4 shows that increasing the ratio of calcium silicate proportionally increased the percentage of adsorption. When the ratio was above 2.5%, the percentage of adsorption exceeded 90%. In the 0.1% to 1.5% range, the curve more resembles a straight line. When the concentration of calcium silicate was greater than 1.5%, the curve gradually flattened out and reached a plateau. This indicates the efficiency of the adsorption was dependent on the concentration of thuringiensin in the mixture. In other word, if the content of thuringiensin in the mixture is increased, the amount of calcium silicate added will be increased to reach more than 90% adsorption efficiency.

Example 3
The Effect of pH on Adsorption of Thuringiensin by Calcium Silicate

The supernatant of the centrifuged broth was filtered with a 0.45 μm membrane filter to remove small particles. The pH of the filtered broth was adjusted to 4.0, 5.0, 6.0, 7.0, 8.0, 9.0, and 10.0 by either 10 N HCl or 10 N NaOH. The 0.5% (w/v) calcium silicate was added. Procedures were followed as described in Example 2, and the remaining amount of thuringiensin in the supernatant was determined.

Figure 5:
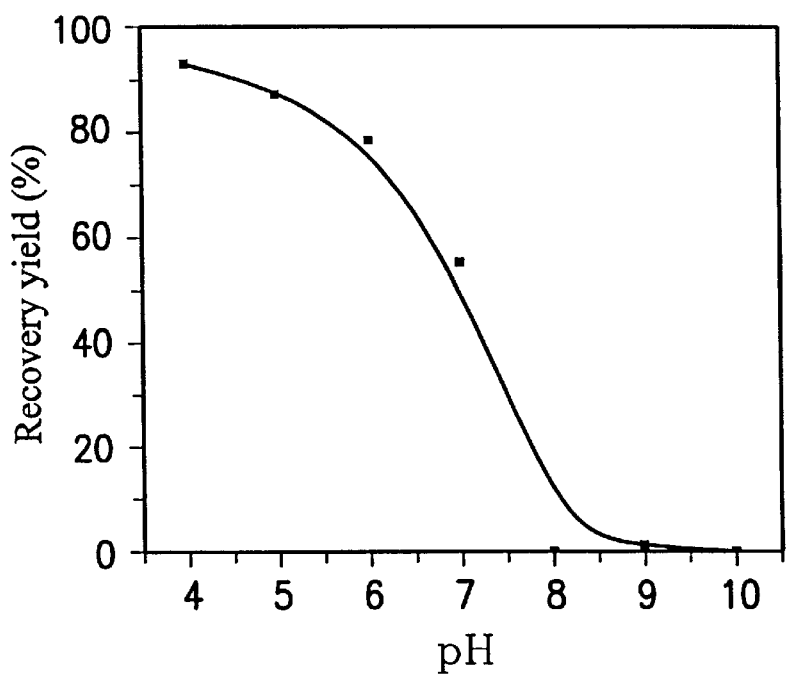
FIG. 5 is a diagram showing the relationship between the pH of broth and the recovery yield.

FIG. 5 shows that under mildly acidic (pH 4 to 5) environments, the recovery yield exceeds 85%. However, the adsorption falls as pH increases from 6 to 9. At pH above 9, particularly, the adsorption becomes close to zero.

Example 4
Selection of Buffer Solutions for Dissociation of Thuringiensin from Calcium Silicate 0.1 g of thuringiensin-bound calcium silicate slurry was mixed with six different buffer solutions (7 ml each) separately, including 0.4 M NaOH, Borate buffer, MEKC running buffer (as depicted in Example 1), $K_2HPO_4$, $NaH_2PO_4$, and $Na_2HPO_4$. After 5 minutes under vortex, the mixtures were centrifuged. The supernatants were analyzed by CE with MEKC mold for determining the amount of thuringiensin dissociated from silicate slurry.

Figure 6:
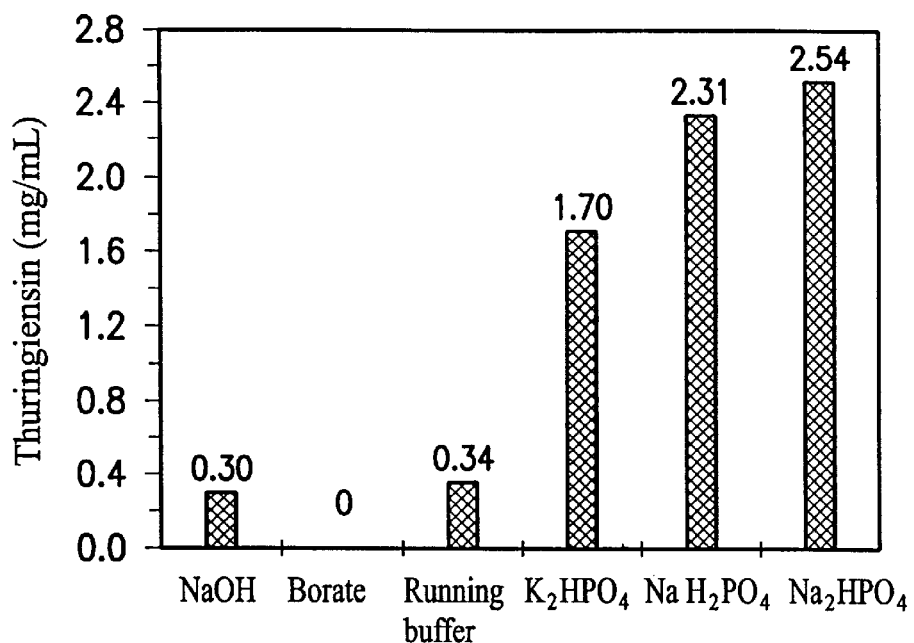
FIG. 6 is a histogram showing the dissociation capacity of six different buffer solutions (same concentration, 0.4 M, as shown in the bottom of the horizontal axis)

Referring to FIG. 6, the dibasic sodium phosphate ($Na_2HPO_4$) shows the greatest dissociation effect compared with the other five buffers. Dibasic sodium phosphate is also better than monobasic sodium phosphate ($NaH_2PO_4$), which implies that an alkaline environment is favorable for the dissociation of thuringiensin.

Figure 7:
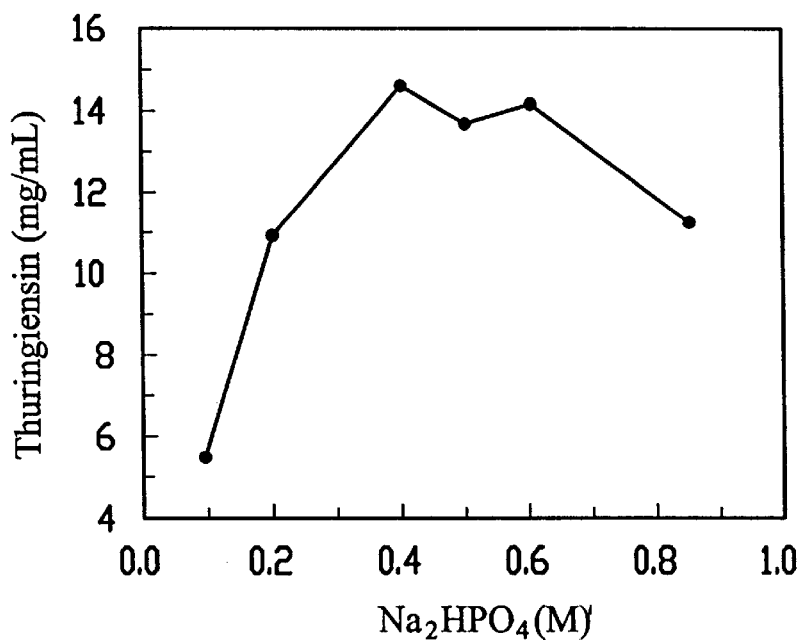
FIG. 7 is a diagram showing the relationship between the amount of thuringiensin dissociation and the concentration of $Na_2HPO_4$.

Example 5
The Effect of Dibasic Sodium Phosphate on the Dissociation of Thuringiensin from Calcium Silicate 0.1 g of thuringiensin-bound calcium silicate slurry was dissolved in 7 ml of $Na_2HPO_4$ of various concentration (0.1, 0.2, 0.4, 0.5, 0.6, and 0.85 M). The mixtures were subjected to vortex for 5 minutes and then centrifuged at 9,000×g for 20 minutes. The supernatant of each concentration was subjected to thuringiensin quantitative analysis. This example was conducted by using different ionic strength of dibasic sodium phosphate to evaluate the efficiency of dissociation. Referring to FIG. 7, the results show that 0.4 M $Na_2HPO_4$ has the greatest efficiency on the dissociation of thuringiensin.

Example 6
Time Course of the Dissociation of Thuringiensin from Calcium Silicate 0.8 g of thuringiensin-bound calcium silicate slurry was divided into 8 tubes equally, and each tube was dissolved in 7 ml of 0.4 M $Na_2HPO_4$. After 5 minutes under vortex, the mixtures were shaken in a water bath shaker (37° C., 120 rpm). The mixtures were removed from the shaker 10-minute periods for centrifugation and assessment of the amount of thuringiensin in the supernatant.

Figure 8:
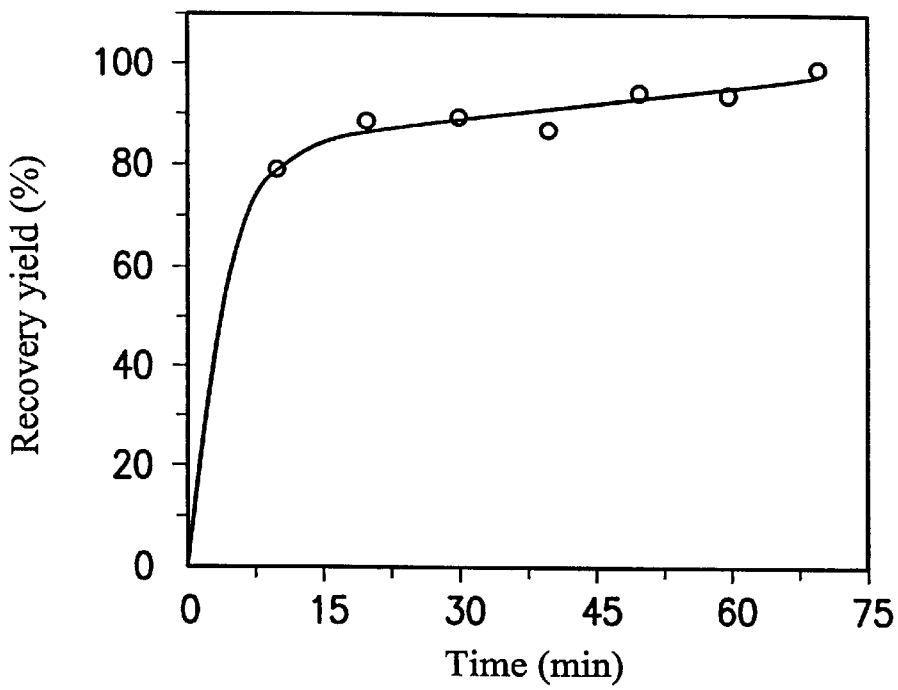
FIG. 8 is a diagram showing the time course of the dissociation by adding 0.4 M $Na_2HPO_4$ in the complex slurry.

FIG. 8 indicates that within 10 minutes of the addition of dibasic sodium phosphate, the recovery (i.e. amount released) was approximately 80%. By prolonging the mixing time to 20 minutes, the recovery yield reached a plateau of approximately 90%.

Example 7
Further Purification and Identification of Thuringiensin

The dissociated thuringiensin solution was then passed through a semi-preparative column. The volume of sample solution was 0.5 ml. The elution buffer used was 50 mM $K_2HPO_4$ at pH 2.8. The thuringiensin peak, appearing between 38 to 42 minutes, was collected. The process was repeated 10 times until all pooled fractions from 38 to 42 minutes were collected. The pH of the pooled fraction was adjusted to 6.0 by $K_3PO_4$ and then concentrated by vacuum evaporator. In order to remove excess $K_3PO_4$ and $K_2HPO_4$ or any other extraneous ions in solution, the concentrated solution was dialyzed by an electrodialyzer (Micro-Acilyzer) with an ion-exchange membrane. A 0.5 M solution of $NaNO_3$ was used as an electrode solution and an AC-220-10 dialysis was installed and operated under a current of 0.05 amperes. The dialyzed solution was lyophilized as pure thuringiensin crystal, which was identified by MS. The mass spectrometric analysis was operated in the negative ion mode of detection and in thioglycerol matrix by fast atomic bombardment (FAB) ionization.

Figure 9:
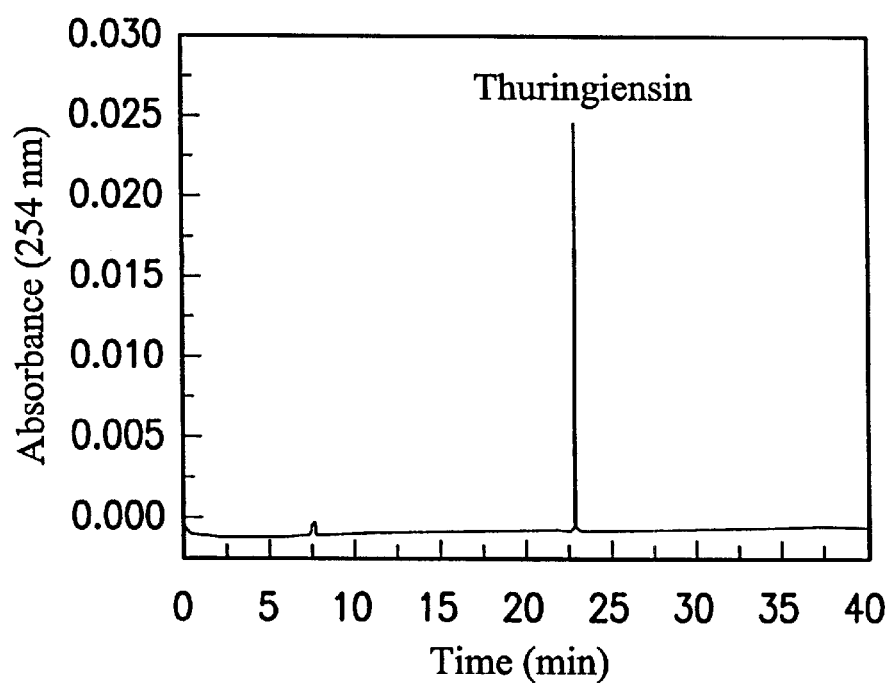
FIG. 9 is an MEKC electropherogram showing the final purified thuringiensin.
Figure 10:
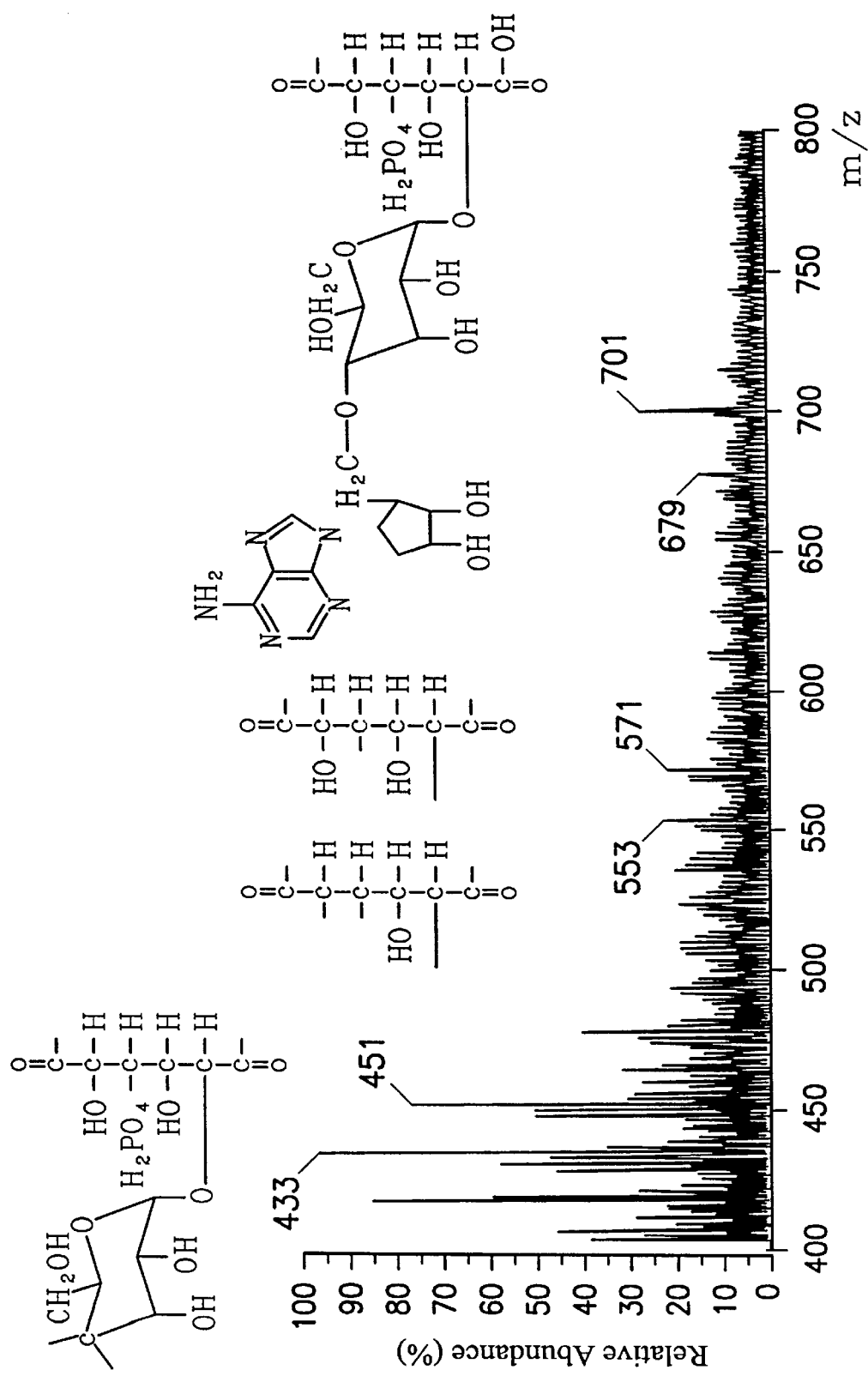
FIG. 10 is an FAB-MS spectrum showing the purified thuringiensin.

FIG. 9 shows a single peak with a quiet baseline (a mall peak at 7.5 min represented the refractive index of the sample solution) in the CE electropherogram, thus denoting the purity of the compound. The results obtained from MS show the matrix ion background and an ion at m/z 701 confirms the thuringiensin molecule (FIG. 10). There are some peaks at m/z 571 and 553, which represent some fragments of dephosphorylated and dehydroxylated glucose moieties. Some lower m/z peaks represent either adenosine or matrix ion background. The high purity was verified by either CE or MS from the above results.

According to the present invention, a two-step process for recovery of thuringiensin is disclosed, comprising adsorbing the thuringiensin from fermentation broth by calcium silicate, and dissociating the thuringiensin by dibasic sodium phosphate. This chemically based method is much more simple and effective than the traditional pore size based filtration methods. Under optimized conditions, the thuringiensin can be adsorbed and then released from the fermentation broth. This, in turn, can be used either as raw material for commercial product or for crystallization as a secondary standard for quantitative assay. For further purification, the semi-preparative and an electrodialysis devices are employed to obtain the thuringiensin with high purity.

While the invention has been particularly shown and described with the reference to the preferred embodiment thereof, it will be understood by those skilled in the art that various changes in form and details may be made without departing from the spirit and scope of the invention.

What is claimed is:

1. A process of purifying thuringiensin, comprising the steps of:
    (a) preparing a sterile and acidic thuringiensin spent fermentation broth;
    (b) performing centrifugation of said thuringiensin fermentation broth;
    (c) adding calcium silicate to the supernatant obtained from step (b), and stirring to form a precipitate of calcium silicate and thuringiensin;

(d) isolating said precipitate by centrifugation;

(e) adding dibasic sodium phosphate into said precipitate and vortexing to dissociate the thuringiensin; and (f) recovering and purifying the thuringiensin dissociated from step (e).

2. The process as claimed in claim 1, wherein the concentration of the thuringiensin in said fermentation broth ranges from 7 to 10 mg/ml.

3. The process as claimed in claim 1, wherein the amount of the calcium silicate added ranges from 0.1% to 5% (w/v).

4. The process as claimed in claim 1, wherein the amount of the calcium silicate added ranges from 1% to 3% (w/v).

5. The process as claimed in claim 1, wherein the pH of said fermentation broth in step (a) ranges between 4 and 6.

6. The process as claimed in claim 1, wherein the centrifugal condition in step (d) is 9,000×g for 30 minutes.

7. The process as claimed in claim 1, wherein the amount of the sodium phosphate added is 20 volumes of said precipitate.

8. The process as claimed in claim 1, wherein the concentration of said sodium phosphate ranges from 0.1 to 0.85 M.

9. The process as claimed in claim 1, wherein the concentration of said sodium phosphate ranges from 0.4 to 0.6 M.

10. The process as claimed in claim 1, wherein the pH of the solution in step (e) ranges between 9.0 and 9.5.

11. The process as claimed in claim 1, wherein the vortexing time in step (e) is 30 minutes.

12. The process as claimed in claim 1, wherein the recovering in step (f) comprises performing centrifugation and then concentrating the supernatant obtained from centrifugation.

13. The process as claimed in claim 12, wherein the centrifugal condition in step (f) is 9,000×g for 30 minutes.

14. The process as claimed in claim 13, wherein the purifying in step (f) comprises purifying the concentrated supernatant by semi-preparative HPLC to obtain an eluant.

15. The process as claimed in claim 14, further comprising the steps of de-salting, concentrating and lyophilizing the eluant purified by HPLC.

* * * * *